United States Patent [19]
Forman

[11] Patent Number: 5,716,208
[45] Date of Patent: Feb. 10, 1998

[54] ORTHODONTIC BRACKET WITH A WATER INSOLUBLE COLORED COATING AND THE ASSOCIATED METHODS OF MANUFACTURE AND USE

[76] Inventor: David Forman, 3008 Bedminster Rd., Perkasie, Pa. 18944

[21] Appl. No.: 642,633

[22] Filed: May 3, 1996

[51] Int. Cl.$^6$ ............................................. A61C 7/00
[52] U.S. Cl. ..................................... 433/8; 433/24
[58] Field of Search ........................... 433/8, 9, 20, 24

[56] References Cited

U.S. PATENT DOCUMENTS

| | | | |
|---|---|---|---|
| 4,129,638 | 12/1978 | Ritze | 264/117 |
| 4,978,521 | 12/1990 | Blue | 424/7.1 |
| 5,074,783 | 12/1991 | Reher | 433/8 |
| 5,454,716 | 10/1995 | Banerjee | 433/20 |

*Primary Examiner*—Cary E. O'Connor
*Attorney, Agent, or Firm*—LaMorte & Associates

[57] ABSTRACT

An improved orthodontic bracket having a bracket body that is either translucent or transparent. The bracket body is coated with a colored layer of water insoluble material that contrasts sharply with the color of teeth. As a result, when the orthodontic brackets are affixed to the teeth, they are easy to see and can be readily aligned by an orthodontic practitioner. The layer of water insoluble material coating the orthodontic brackets is highly soluble in alcohol. As a result, the color coating can be removed from the orthodontic brackets by rinsing the mouth with a mouth wash that contains alcohol. As such, after the orthodontic practitioner has applied the orthodontic brackets to the teeth, the colored layer of material can be dissolved away leaving only the translucent or transparent bracket body behind.

18 Claims, 4 Drawing Sheets

ORTHODONTIC BRACKET WITH A WATER INSOLUBLE COLORED COATING AND THE ASSOCIATED METHODS OF MANUFACTURE AND USE

BACKGROUND OF THE INVENTION

1. Field of the Invention

The present invention relates to orthodontic brackets and the associated methods of manufacturing and applying orthodontic brackets. More specifically, the present invention relates to orthodontic brackets having colored coatings that add to the aesthetics of the orthodontic brackets and are useful in the application of the orthodontic brackets to the teeth.

2. Description of the Prior Art

Orthodontic brackets are the components that are mechanically or adhesively affixed to teeth when a person receives orthodontic braces. The orthodontic brackets support an orthodontic arch wire that spans across the teeth and applies a corrective force to the teeth. Each orthodontic bracket has a smooth surface designed to abut against the surface of a tooth and an opposite surface designed to engage the arch wire. As an arch wire is stretched across the teeth, the forces of the arch wire are evenly applied to the teeth via the orthodontic brackets. The orthodontic brackets and arch wire are applied in such a manner so that the forces of the arch wire act to alter the orientation of the teeth into a more bio-mechanically correct and/or aesthetically pleasing pattern.

Over the years there have been many different types of orthodontic brackets developed. The original orthodontic brackets were metal. As such, when a person with braces smiled, the metal brackets were highly noticeable. In an attempt to improve the aesthetics of orthodontic brackets, the art moved toward plastic and ceramic orthodontic brackets that can be manufactured to be translucent or nearly transparent. Such prior art orthodontic brackets are exemplified by U.S. Pat. No. 5,078,596 to Carberry et al., entitled ORTHODONTIC BRACKET AND ASSOCIATED FABRICATING METHOD.

When a modern translucent orthodontic bracket is placed on a tooth, it is purposely designed to be difficult to see. This aesthetic design, however, does present significant problems to the orthodontic practitioner who is applying the orthodontic brackets to the teeth. When orthodontic brackets are applied to the teeth, the orthodontic brackets must be aligned properly with respect to each other and with respect to the teeth on which the orthodontic brackets are being applied. If the orthodontic brackets are not aligned properly, the arch wire that passes across the various orthodontic brackets will not apply the proper forces to the teeth. As a result, the misaligned orthodontic brackets will not produce the desired corrective change and may even produce an adverse change in the orientation of the teeth.

Since many modern translucent orthodontic brackets are designed to be difficult to see in the mouth, it is often difficult for an orthodontic practitioner to properly position such orthodontic brackets onto the teeth. Even if one translucent orthodontic bracket is properly applied to a first tooth, it is difficult for the orthodontic practitioner to properly apply a second orthodontic bracket on an adjacent tooth and align it with the first. This is the case because the edges of the orthodontic bracket are hard to identify after the orthodontic bracket is applied to a tooth. If an orthodontic bracket is joined to a tooth in a misaligned orientation, then the orthodontic bracket must be removed and reapplied. Such corrective procedures prolong the application procedure and can cause damage to the enamel of a tooth.

In an attempt to solve the problems in aligning orthodontic brackets, temporary colors have been added to the orthodontic brackets prior to their application into the mouth. Such prior art coloring techniques are exemplified by U.S. Pat. No. 5,074,783 to Reher, entitled ORTHODONTIC BRACKET COATED WITH WATER SOLUBLE DYE. In the Reher patent, a water soluble dye coats the surfaces of an orthodontic bracket that touch the interior of the mouth. In theory, the presence of the dye makes the orthodontic brackets temporarily more easy to see. However, in practice, the water soluble dye used on the orthodontic brackets begin to run the second that dye contacts saliva within the mouth. As a result, the ink runs throughout the mouth thereby causing the shade of the entire mouth to match that of the orthodontic bracket. The edges of the orthodontic bracket therefore again becomes hard to distinguish within the mouth and the use of the water soluble dye becomes self-defeating. Furthermore, at the end of the orthodontic bracket application procedure, the patient's saliva, tongue and gums are temporarily tinted with the ink, thereby adding to the psychological discomfort of the patient who must adjust to the newly applied orthodontic braces.

A further disadvantage of prior art devices, such as that described in the Reher patent, is that the water soluble dye used on the orthodontic brackets is placed on the surfaces of the orthodontic bracket that contact the inside surfaces of the mouth. As a result, when the lips pass over the orthodontic brackets, the lips act to wipe the water soluble dye off of the orthodontic brackets. The water soluble dye therefore remains on each bracket only for a short time and often the dye is completely gone before the orthodontic bracket application procedure is over. When applying orthodontic brackets, each orthodontic brackets is aligned not only with the tooth but also to the orthodontic brackets already applied to adjacent teeth. Consequently, in order to assist an orthodontic practioner to align the orthodontic brackets, each orthodontic bracket in the mouth must remain clearly visible until all of the orthodontic brackets have been applied. The dye therefore must remain on the orthodontic brackets until after the entire application procedure is complete.

Many patients who have just received orthodontic brackets tend to develop sores on the inside of their mouths as the inside surfaces of the mouth rub against the protruding orthodontic brackets. The sores often persist until the mouth adapts to the presence of the orthodontic brackets. Since, in the prior art, the sores that develop within the mouth rub against the same surfaces of the orthodontic brackets that are coated with dye, great care must be used in the selection of colored dye in order to ensure that the dye will not cause adverse effects, such as an infection, in an open sore or prohibit the healing of an open sore.

In many orthodontic applications, rubber bands are used within the mouth. Although translucent rubber bands have been developed that are not conspicuous, brightly colored vanity rubber bands are becoming increasingly popular. Using this same logic, it can be surmised that although the trend in orthodontic brackets has been to make the orthodontic brackets as inconspicuous as is possible, certain patients may prefer orthodontic brackets that are brightly colored or at least are brightly colored for a desired period of time. Obviously, if a manufacturer is manufacturing vanity orthodontic brackets that are brightly colored, water soluble dyes such as that used in the Reher patent can not be used. Rather, a need exists for an orthodontic bracket the can be selectively colored and that color will remain without running until the patient desires to remove the color.

In view of the needs that exist in the art and the disadvantages of the devices that already exist in the art, it is an objective of the present invention to provide orthodontic brackets that are translucent, yet are coated with a water insoluble colorant that can be selectively removed at any time after the application of the orthodontic brackets to the teeth.

It is also an objective of the present invention to provide a method of manufacturing orthodontic brackets that are translucent but are temporarily colored with a water insoluble colorant that can be selectively removed at ant time.

It is yet another objective of the present invention to provide a method of applying orthodontic brackets to teeth, wherein the orthodontic brackets are translucent after being applied to the teeth but are not translucent while being initially applied to the teeth and do not contain water soluble dye.

It is still yet another objective of the present invention to provide an orthodontic bracket that assists in the healing of sores that may develop in the mouth due to the physical presence of the orthodontic brackets.

It is yet still another objective of the present invention to provide a means of selectively coloring any existing orthodontic bracket for vanity purposes, wherein the applied color can be selectively removed and/or changed at any time.

SUMMARY OF THE INVENTION

The present invention is an improved orthodontic bracket. In one embodiment, the orthodontic bracket has a bracket body that is either translucent or transparent. The bracket body is coated with a colored layer of water insoluble material that contrasts sharply with the color of teeth. As a result, when the orthodontic brackets are affixed to the teeth, they are easy to see and can be readily aligned by an orthodontic practitioner. The layer of water insoluble material coating the orthodontic brackets is highly soluble in alcohol. As a result, the color coating can be removed from the orthodontic brackets by rinsing the mouth with a mouth wash that contains alcohol. As such, after the orthodontic practitioner has applied the orthodontic brackets to the teeth, the colored layer of material can be dissolved away leaving only the translucent or transparent bracket body behind. Consequently, the present invention orthodontic bracket provides a means for an orthodontic practitioner to apply translucent or transparent brackets to the teeth without the orthodontic practitioner having difficulty seeing the orthodontic brackets and aligning the orthodontic brackets during the application procedure.

Furthermore, the colored material used to coat the orthodontic brackets preferably has antibacterial properties that assist in healing of sores in the mouth created by the physical presence of the orthodontic brackets.

In a second embodiment, the orthodontic bracket has an opaque bracket body that can be metal, plastic or ceramic. The bracket body is coated with a colored layer of water insoluble material in order to selectively color the bracket bodies. As a result, when the orthodontic brackets are affixed to the teeth, they are easy to see. The layer of water insoluble material coating the orthodontic brackets is highly soluble in alcohol. As a result, the color coating can be removed from the orthodontic brackets by rinsing the mouth with a mouth wash that contains alcohol. As such, the color on the orthodontic brackets can be removed at any time.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Figure 1:
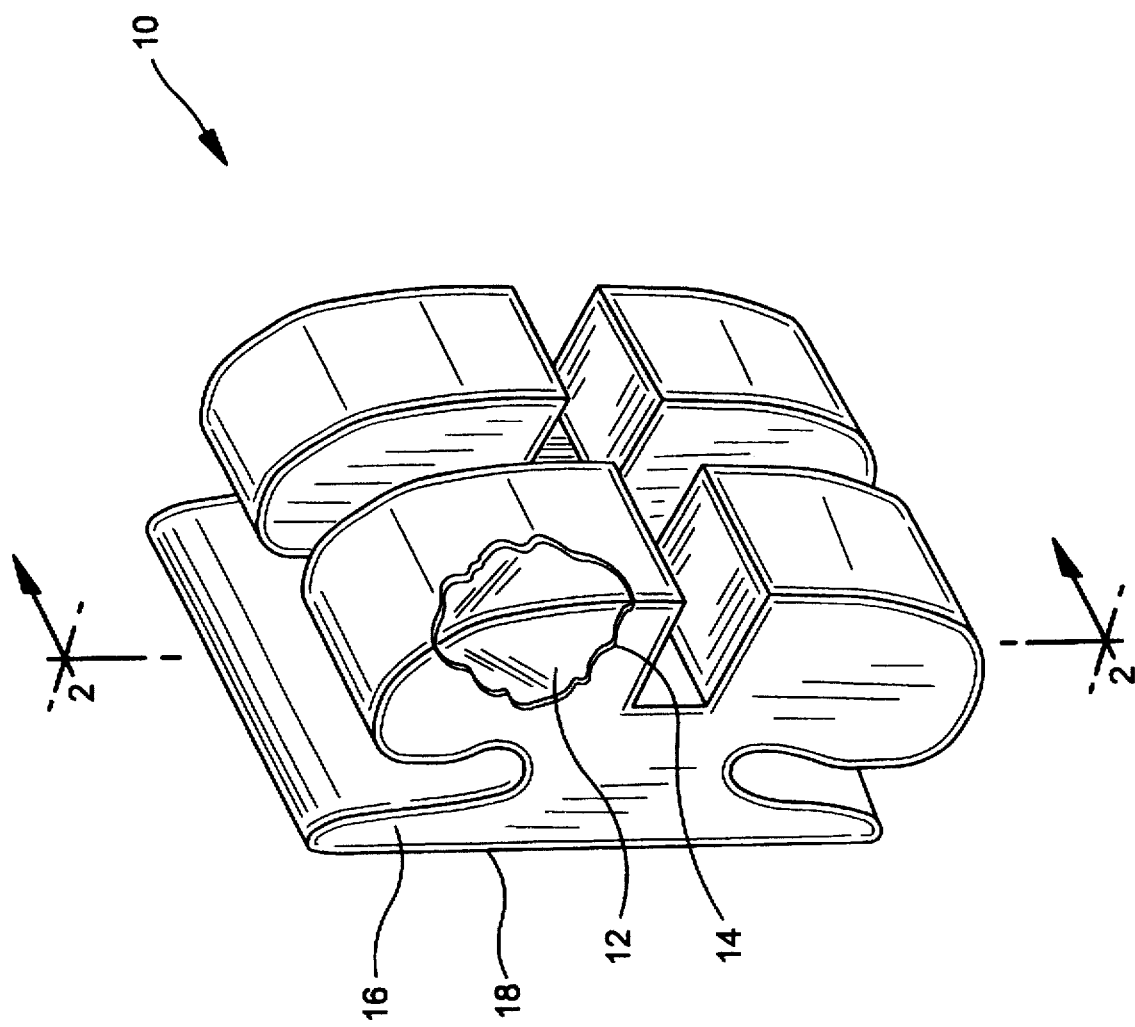
FIG. 1 is a perspective view of one preferred embodiment of the present invention orthodontic bracket.
Figure 2:
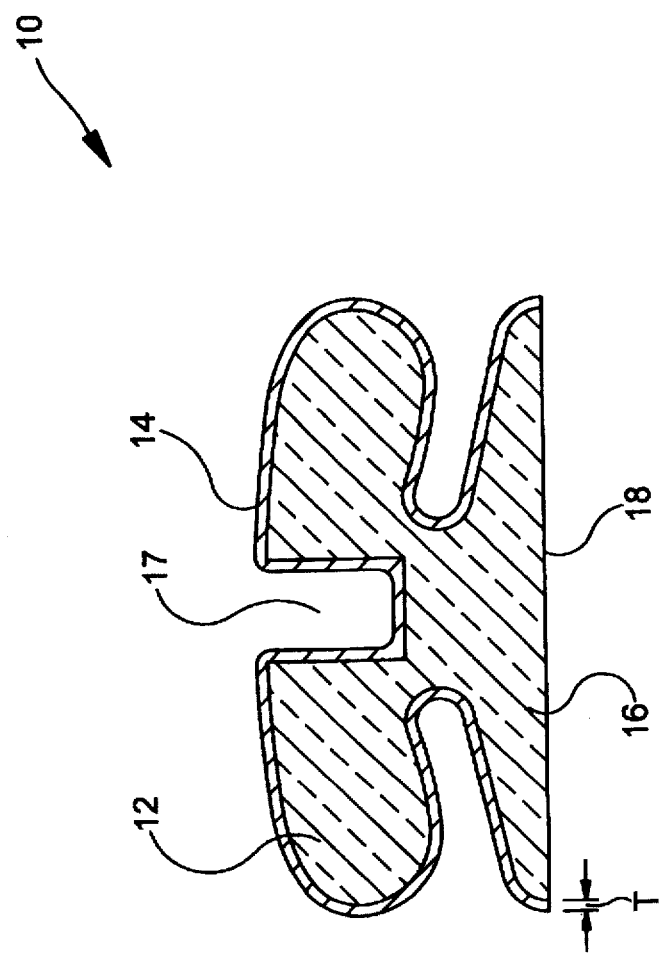
FIG. 2 is a cross-sectional view of the embodiment of FIG. 1, viewed along section line 2—2.

Referring to FIG. 1 and FIG. 2, an orthodontic bracket 10 is shown in accordance with the present invention. The orthodontic bracket 10 consists of a bracket body 12 coated with an outer coating 14. The bracket body 12 can be any translucent or transparent orthodontic bracket used in the practice of orthodontic care. As such, it should be understood that the size and shape of the bracket body 12 is not critical to the practice of the invention. The bracket body 12 has a base region 16. The base surface 18 that defines one side of the base region 16 is the surface that abuts against a tooth after the bracket body 12 is applied to the tooth. Although the present embodiment shows a bracket body 12 designed to be adhesively affixed to a tooth, such an embodiment is merely exemplary and it should be understood that bracket bodies designed to mechanically attach to teeth can also be used.

The outer coating 14 coats most every surface of the bracket body 12 except for the base surface 18 that joins to a tooth. The outer coating 14 is colored a color that contrasts well with both the ivory white color of teeth and the pink-red color of gums, the tongue and the inside of the mouth. For instance, the outer coating 14 can be colored blue, green, black, fluorescent orange or any other contrasting color. The presence of the outer coating 14 on the bracket body 12 makes the overall bracket body 12 easy to see when inside the mouth. Since the color of the outer coating 14 contrasts with the ivory white of the teeth and the pink-red colors of the tongue, mouth and gums, an orthodontic practitioner can easily identify the orthodontic bracket 10 even if the orthodontic bracket 10 is inadvertently dropped in the mouth during the application procedure. The contrasting color of the outer coating 14 also makes the orthodontic brackets 10 easy to align on the teeth because the edges of the orthodontic bracket 10 are readily discernable and therefore are much easier to align by eye.

The outer coating 14 that coats the bracket body 12 is water insoluble, yet is highly alcohol soluble. As a result, the outer coating 14 will not ordinarily dissolve when placed into the mouth. The water insolubility of the outer coating prevents the color from running into the mouth and changing the tint of the saliva. In the preferred embodiment, the outer coating 14 is a compound that includes an colorant. The colorant can be any pigmented particle that itself does not readily dissolve in water. The colorant can be emulsified within the outer coating 14 or can be dissolved within the outer coating 14. The colorant is preferably pigment particles encapsulated within the outer coating 14. As such, the pigment particles themselves need not be dissolvable in alcohol. Rather, the pigment particles are rinsed away as the outer coating 14 dissolves in an alcohol rinse. However, in an alternative embodiment, the colorant can be a color salt, such as an ethyl auramine salt, or a disazo salt that is dissolved within the composition of the outer coating 14.

Such color salts are not substantially soluble in water but are highly soluble in alcohol or alcohol-water mixtures. The use of color salts is merely exemplary and it should understood that any known non-toxic colorant that is alcohol soluble and water insoluble can also be used.

In addition to a colorant, the outer coating 14 may also contain an antibacterial agent that is also not substantially water soluble but is highly alcohol soluble. The antibacterial agent is preferably selected from a group consisting of halogenated diphenyl ethers, halogenated salicylanilides, hydrophilic polymers, benzoic esters, halogenated carbanilides, phenol compounds, phenol homologs, mono halophenols, poly-alkyl haleophenols, resorcinol compounds, and bisphenolic compounds.

In the preferred embodiment, the antibacterial agent is 2, 4, 4'-trichloro-21'-hydroxy-diphenyl ether. 2, 4, 4'-trichloro-21'hydroxy-diphenyl ether is a halogenated diphenyl ether commonly referred to by the tradename Triclosan. Triclosan is a substantially water insoluble, noncationic antibacterial agent commonly used as an antibacterial and antiplaque agent in mouthwash compositions containing alcohol and other compounds applied within the mouth.

Depending upon the properties of the colorant used and the antibacterial compound used, the outer coating may also include an inert binding agent, such as certain organic waxes, ester polymers, polyamide resins, protein hydrolyzate derivatives, acyl amide derivatives of polypeptide compounds and similar binding agents. Such binding agents are highly soluble in organic solvents such as alcohol but are substantially not soluble in water.

From the above, it should be understood that the outer coating 14 can be an alcohol soluble colorant, a colorant/antibacterial combination, a colorant/antibacterial/binder combination or a colorant/binder combination. Depending upon the physical characteristics of the outer coating compound, the outer coating compound can be thinned with alcohol until it is at a consistency that enables the compound to be applied to the bracket body 12. The thickness T (FIG. 1) of the outer coating 14 on the bracket body 12 depends upon how long the outer coating 14 is to last within the mouth. Although the outer coating 14 is not water soluble, the outer coating 14 will experience wear due to the contact between the mouth and the orthodontic brackets 10. In a preferred embodiment, the thickness T of the outer coating 14 is selected so that the outer coating will last from one to ten days if the mouth is not exposed to alcohol. However, at such a thickness T, the outer coating 14 can be removed in less than one minute by rinsing the mouth with a solution containing at least ten percent alcohol.

In the preferred embodiment, the outer coating is made from an emulsion of pigment particles in Triclosan. Initially, the Triclosan is dissolved in alcohol and mixed with pigment particles. The mixture is reduced to a high viscosity and applied to the orthodontic bracket body 12, wherein the remaining alcohol quickly evaporates and a solid colored outer coating 14 remains. Since the outer coating 14 is made from compounds that do not dissolve in water, the outer coating does not dissolve in the mouth until the mouth is rinsed with mouthwash that contains alcohol. This provides the orthodontic practitioner with ample time to align and attach each orthodontic bracket 10 to each tooth without concern of the color dissolving off of the orthodontic brackets. Once the orthodontic bracket application procedure is complete, the orthodontic practioner has the option of telling the patient to rinse with mouthwash containing alcohol, leaving the outer coating 14 in place to wear away over time or leaving the outer coating 14 to rinsed away by the patient at a later date. Once the outer coating 14 wears away or is dissolved away, only the transparent bracket body 12 remains. As a result, an aesthetically pleasing transparent orthodontic structure is provided without the transparent nature of the bracket bodies acting as a disadvantage during the application procedure.

As can be seen from FIG. 2, the outer coating 14 does not cover the base surface 18 of the orthodontic bracket 10. As a result, the outer coating 14 does not interfere with the adhesive connection and/or mechanical connection used to couple the orthodontic bracket 10 to the surface of a tooth. Depending upon the thickness T of the outer coating 14, the outer coating can also not be applied to the arch wire groove 17 in the center of the orthodontic bracket 10. As a result, the outer coating would not interfere with the application of an arch wire to the orthodontic bracket 10.

Figure 3:
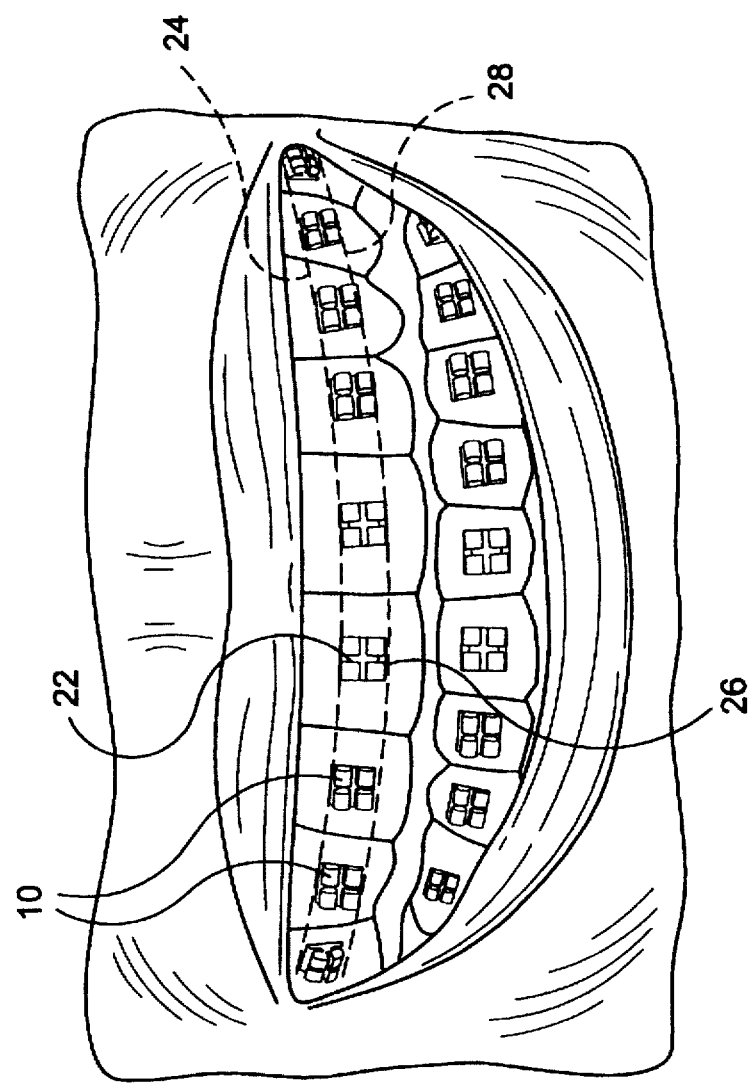
FIG. 3 shows a plurality of orthodontic brackets applied to teeth to illustrate the advantages of the present invention orthodontic bracket.

Referring to FIG. 3, it can be seen that when an orthodontic practitioner places orthodontic brackets 10 onto the teeth, the practitioner-attempts to align the orthodontic brackets 10 so that each bracket is properly vertically aligned on each tooth. Furthermore, each orthodontic bracket 10 is aligned with the orthodontic brackets 10 on the adjacent teeth. As such, the top edge 22 of each orthodontic bracket 10 falls along a first common imaginary alignment line 24. Similarly, the bottom edge 26 of each orthodontic bracket 10 falls along a second common imaginary line 28. The side edges of each orthodontic bracket 10 are aligned to be perpendicular to both the first and second imaginary alignment lines 24, 28. By having highly visible orthodontic brackets 10, it is much easier for an orthodontic practitioner to identify the edges of the orthodontic bracket and envision the imaginary alignment lines 24, 28 across the row of teeth. It therefore becomes much easier for an orthodontic practitioner to properly position the orthodontic brackets in the correct orientation on the teeth.

As has been previously stated, a orthodontic practioner may opt to leave the outer coating 14 in place even after the orthodontic brackets 10 have been applied to all the teeth. One reason for leaving the outer coating 14 intact is for the sake of patient vanity. Most patients who receive orthodontic brackets are preadolescents and adolescents. At this age some patients may think it to be aesthetically pleasing that the orthodontic brackets 10 are brightly colored or otherwise sharply contrast with the patient's teeth. The patient would then have several days to show off the colored orthodontic brackets 10 until the color faded away and the orthodontic brackets 10 became translucent. If the patient did not want to wait for the outer coating to fade wear away, the patient can rinse with mouthwash that contains alcohol at any time to dissolve away the outer coating 14. For this reason, it should be understood that in certain embodiments, the bracket body below the outer coating 14 need not be transparent of translucent. Rather, opaque metal, ceramic or plastic bracket bodies can be used, wherein the outer coating serves only to add a temporary desired color to the orthodontic brackets 10.

Another advantage to leaving the outer coating 14 in place is that the outer coating can contain an antibacterial agent such as Triclosan. As the interior of the mouth wears against the orthodontic brackets 10, sores may develop on the inside of the mouth. However, as the interior of the mouth wears against the orthodontic brackets 10, the outer coating 14 is slowly worn away, thereby releasing small amounts of the antibacterial agent. The antibacterial agent acts as an antiseptic, thereby repeatedly cleaning the areas of the sores until the sores heal and the mouth adapt to the presence of the orthodontic brackets 10.

Figure 4:
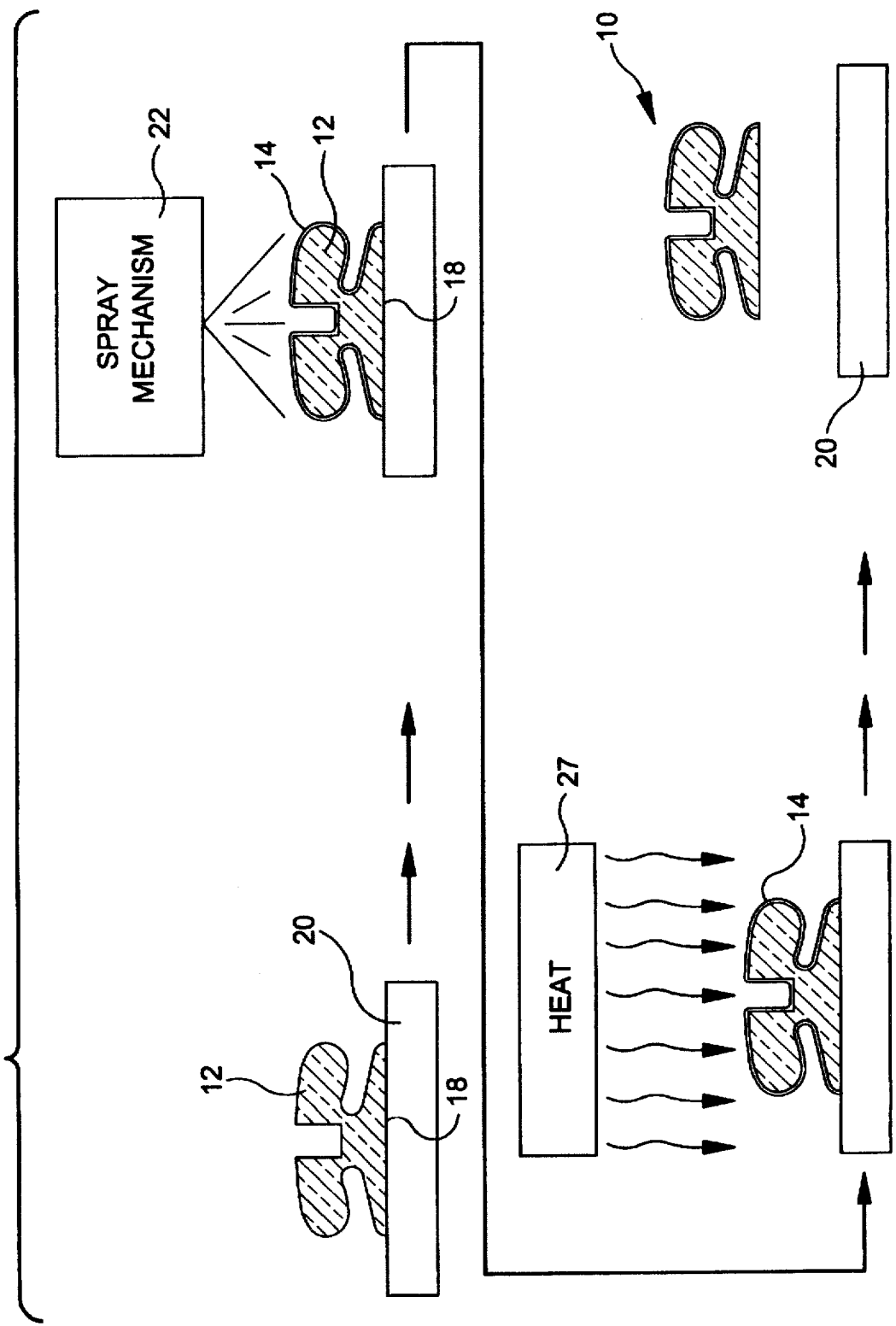
FIG. 4 is a schematic diagram illustration of one method of manufacturing the present invention orthodontic bracket.

Referring to FIG. 4, a preferred manufacturing process for the present invention orthodontic bracket 10 is shown. First, transparent or translucent bracket bodies 12 are either bought from a supplier or are manufactured using known prior art processes. The bracket bodies 12 are then placed on a disposable support 20 in an orientation so that the base surface 18 of the bracket bodies 12 lays against the disposable support 20. The bracket bodies 12 are then brought under a spray coating mechanism 22 that applies the outer coating 14 to all surfaces of each bracket body 12 except for the unexposed base surface 18. The outer coating 14 is then dried in a heated curing chamber 27 depending upon the composition of the material applied as the outer coating 14 and thickness of the outer coating 14.

After curing, the orthodontic brackets 10 are removed from the disposable support 20 and are ready for use. Since the base surface 18 of each orthodontic bracket 10 is shielded from the spray application of the outer coating 14, the base surface 18 is free of contaminants and is ready to be directly bonded to the surface of a tooth using known bonding techniques.

Although it is preferred that the outer coating 14 be applied by a manufacturer, it should be understood that the outer coating material can be sold separately and can be applied to the teeth by the orthodontic practitioner or by the patient himself/herself. In such applications, the material of the outer coating 14 can be painted onto brackets with a brush, thereby enabling the coloring or the orthodontic brackets to be customized or otherwise selectively altered.

It will be understood that the embodiments of the present invention specifically described are merely exemplary and that many modifications can be made to the exemplary embodiments by a person skilled in the art. For instance, the outer coating can be applied to a transparent or translucent bracket body using any known method of application, including spraying, dipping, deposition and painting. Sections of the bracket body where it would be desirable to not apply an outer coating can be masked during the application of the outer coating. All such variations and modifications are intended to be included within the scope of the present invention as defined by the appended claims.

What is claimed is:

1. A device comprising:
   an orthodontic bracket body having a base surface and a plurality of other exterior surfaces;
   a layer of colored material coating at least one of said exterior surfaces, wherein said layer of colored material is not substantially water soluble and is highly alcohol soluble.

2. The device according to claim 1, wherein said layer of colored material includes a colorant and an antibacterial agent.

3. The device according to claim 2, wherein said antibacterial agent is selected from a group consisting of halogenated diphenyl ethers, halogenated salicylanilides, hydrophilic polymers, benzoic esters, halogenated carbanilides, phenol compounds, phenol homologs, mono halophenols, poly-alkyl haleophenols, resorcinol compounds, and bisphenolic compounds.

4. The device according to claim 2, wherein said antibacterial agent includes 2, 4, 4'-trichloro-2 1'-hydroxy-diphenyl ether.

5. The device according to claim 2, wherein said colorant includes pigment particles emulsified in said antibacterial agent.

6. The device according to claim 1, wherein said layer of colored material includes a colorant and a binding agent.

7. The device according to claim 1, wherein said layer of colored material includes an alcohol soluble color salt.

8. The device according to claim 1, wherein said layer of colored material includes an alcohol soluble antibacterial agent.

9. The device according to claim 1, wherein said layer of colored material coats substantially all of said exterior surfaces except for said base surface.

10. The device according to claim 1, wherein said orthodontic bracket body is substantially translucent.

11. The device according to claim 1, wherein said orthodontic bracket body is substantially transparent.

12. The device according to claim 1, wherein said layer of colored material is colored a color that contrasts with the color of teeth.

13. The device according to claim 1, wherein said layer of colored material is colored a color that contrasts with the color of gums within the mouth.

14. A method of manufacturing an orthodontic bracket comprising the steps of:
   providing an orthodontic bracket body having a base surface and a plurality of other exterior surfaces; and
   coating at least one of said exterior surfaces with a layer of material that is not substantially water soluble and is highly alcohol soluble.

15. The method according to claim 14, wherein said layer of material includes a colorant and an antibacterial agent.

16. The method according to claim 14, wherein said layer of material includes a halogenated diphenyl ether.

17. The method according to claim 14, wherein said layer of material includes pigment particles emulsified in an alcohol soluble compound.

18. A method of applying a plurality of orthodontic brackets to teeth, wherein each of said orthodontic brackets is coated with a colored layer of material that is water insoluble and contrasts in color with the color of the teeth, said method comprising the steps of:
   attaching said orthodontic brackets to the teeth in an aligned configuration; and
   dissolving away said colored layer of material within the mouth by rinsing the mouth with a rinse containing alcohol.

* * * * *